United States Patent
Jain

(10) Patent No.: US 9,320,595 B2
(45) Date of Patent: Apr. 26, 2016

(54) APPARATUS, SYSTEM AND METHOD FOR PROVIDING A COATING FOR AN IMPLANTABLE LENS

(71) Applicant: Abbott Medical Optics Inc., Santa Ana, CA (US)

(72) Inventor: Rakhi Jain, Fort Worth, TX (US)

(73) Assignee: Abbott Medical Optics Inc., Santa Ana, CA (US)

( * ) Notice: Subject to any disclaimer, the term of this patent is extended or adjusted under 35 U.S.C. 154(b) by 15 days.

(21) Appl. No.: 14/161,469

(22) Filed: Jan. 22, 2014

(65) Prior Publication Data

US 2014/0135922 A1    May 15, 2014

Related U.S. Application Data

(63) Continuation of application No. 13/020,616, filed on Feb. 3, 2011, now abandoned.

(51) Int. Cl.
*A61F 2/14* (2006.01)
*A61F 2/16* (2006.01)
*A61L 27/34* (2006.01)

(52) U.S. Cl.
CPC ............... *A61F 2/1613* (2013.01); *A61L 27/34* (2013.01); *A61L 2300/452* (2013.01); *A61L 2430/16* (2013.01)

(58) Field of Classification Search
CPC .... G02B 1/043; A61L 27/16; A61L 2430/16; C08L 83/04; A61F 2/16
See application file for complete search history.

(56) References Cited

U.S. PATENT DOCUMENTS

| | | | |
|---|---|---|---|
| 4,170,043 A * | 10/1979 | Knight et al. | 623/6.57 |
| 4,713,072 A * | 12/1987 | Bowald | 623/6.13 |
| 5,358,520 A | 10/1994 | Patel | |
| 5,951,565 A | 9/1999 | Freeman | |
| 7,118,596 B2 | 10/2006 | Zadno-Azizi et al. | |
| 2002/0183844 A1 | 12/2002 | Fishman et al. | |
| 2004/0106993 A1 | 6/2004 | Portney | |
| 2005/0251254 A1 | 11/2005 | Brady et al. | |
| 2006/0259139 A1 | 11/2006 | Zadno-Azizi et al. | |
| 2008/0161913 A1 | 7/2008 | Brady et al. | |
| 2008/0161914 A1 | 7/2008 | Brady et al. | |
| 2010/0074942 A1 | 3/2010 | Ratner et al. | |
| 2011/0251685 A1 * | 10/2011 | Chu | B29D 11/023 623/6.43 |

OTHER PUBLICATIONS

International Search Report and Written Opinion for Application No. PCT/US2012/023457, mailed on May 30, 2012, 16 pages.
Liu, H., et al., "Polylactide-glycoli Acid and Rapamycin Coating Intraocular Lens Prevent Posterior Capsular Opacification in Rabbit Eyes," Graefe's Archive for Clinical and Experimental Opthamology, 2009, vol. 247 (6), pp. 801-807.

* cited by examiner

*Primary Examiner* — David H Willse
*Assistant Examiner* — Tiffany Shipmon
(74) *Attorney, Agent, or Firm* — Abbott Medical Optics Inc.

(57) ABSTRACT

An apparatus, system and method for coating an implantable lens. The apparatus, system and method may include at least one coating layer applied to at least one surface of the optic of the implantable lens, wherein the coating layer at least partially protects the optic at least during the implantation, and wherein the coating layer is removable following implantation. The coating layer may include a lubricant and/or medication and may be in the form of a biodegradable polymer and/or a film.

16 Claims, 8 Drawing Sheets

APPARATUS, SYSTEM AND METHOD FOR PROVIDING A COATING FOR AN IMPLANTABLE LENS

CROSS-REFERENCES TO RELATED APPLICATIONS

This application is a continuation application and claims priority to U.S. application Ser. No. 13/020,616 of the same name, filed on Feb. 3, 2011, the entire contents of which are hereby incorporated by reference in its entirety for all purposes as if fully set forth herein.

FIELD OF THE INVENTION

The instant disclosure relates to implantable lenses, and, more particularly, to an apparatus, system and method for providing a one or more coatings or films for an implantable lens.

BACKGROUND OF THE INVENTION

Surgery on the human eye has become commonplace in recent years. Many patients pursue eye surgery as an elective procedure, such as to avoid the use of contacts or glasses, and other patients may find it necessary to pursue surgery to correct an adverse condition in the eye. Such adverse conditions may include, for example, cataracts or presbyopia, as well as other conditions known to those skilled in the art that may negatively affect elements of the eye. For example, a cataract may increase the opacity of the natural lens of the eye, causing impaired vision or blindness. Correction of such adverse conditions may be achieved by surgically removing a cloudy or diseased lens in the patient's eye and replacing it with an artificial lens, known as an intraocular lens (IOL).

The anatomy and physiology of the human eye is well understood. Generally speaking, the structure of the human eye includes an outer layer formed of two parts, namely the cornea and the sclera. The middle layer of the eye includes the iris, the choroid, and the ciliary body. The inner layer of the eye includes the retina. The eye also includes, physically associated with the middle layer, a crystalline lens that is contained within an elastic capsule, referred to herein as the lens capsule, or capsular bag.

Image formation in the eye occurs by entry of image-forming light to the eye through the cornea, and refraction by the cornea and the crystalline lens to focus the image-forming light on the retina. The retina provides the light sensitive tissue of the eye.

Functionally, the cornea has a greater, and generally constant, optical power in comparison to the crystalline lens. The power of the crystalline lens, while smaller than that of the cornea, may be changed when the eye needs to focus at different distances. This change, or "accommodation," is achieved by changing the shape of the crystalline lens. Accommodation, as used herein, includes the making of a change in the focus of the eye for different distances. For example, in order to change the shape of the crystalline lens for accommodation, the ciliary muscles may relax to cause ligaments (zonules) that support the crystalline lens to relax, thereby allowing the crystalline lens to become more rounded.

The iris operates to change the aperture size of the eye. More specifically, the diameter of the incoming light beam is controlled by the iris, which forms the aperture stop of the eye, and the ciliary muscles may contract, as referenced above, to provide accommodation in conjunction with any needed change in the size of the aperture provided by the iris. The opening, or aperture, in the iris is called the pupil.

Correction of defects or degradation in the aspects of the eye may occur surgically, as mentioned above, or non-surgically. In a simple example, it is common to wear glasses or contact lenses to improve vision by correcting myopic (near-sighted), hyperopic (far-sighted) and astigmatic eyesight. Rather than relying on glasses or contacts, elective laser refractive surgery, or other eye surgery, may serve to improve the refractive state of the eye, and may thereby decrease or eliminate dependence on glasses or contact lenses. Additional surgeries may include various methods of surgical remodeling of the cornea, or cataract surgery, for example. Surgery may also serve to implant an IOL, either in addition to the crystalline lens, which addition is referred to as a phakic IOL, or upon removal of the crystalline lens, which replacement is referred to as a pseudophakic IOL.

An IOL may be implanted in the eye, for example, as a replacement for the natural crystalline lens after cataract surgery, or to alter the optical properties of an eye in which the natural lens remains. IOLs often include an optic, and may preferably include at least one flexible fixation member, or haptic, that extends from the optic and becomes affixed in the eye to secure the lens in proper position to provide the desired vision correction. The optic typically includes an optically clear lens, and the opacity of the haptic may vary.

More specifically, the IOL may consist of a small plastic lens with haptics comprised of plastic side struts. The IOL may generally be made of an inflexible material, such as polymethyl methacrylate (PMMA), for example, or of a flexible material. The IOL may be a fixed monofocal lens matched to distance vision, or a multifocal lens that provides the recipient with multiple-focused vision at far and reading distances, for example. The IOL may also be a toric IOL to correct for astigmatism or an accommodating IOL that provides the recipient with vision at all distances (far, intermediate, and near) by moving and/or changing shape with the use of the muscles of the eye.

Flexible, softer materials may be preferred for the optic of the IOL, such as in order to allow for greater deformation, and thereby increased power change, in vivo. That is, the softer, more flexible materials mimic the mechanical properties of the natural lens material at a young age. However, with softer materials comes the concern that the optic may be more easily damaged, particularly during surgical insertion through a surgical incision and in placement and manipulation of the IOL in the capsular bag.

Implantation of an IOL into the eye involves making this surgical incision in the eye. Those skilled in the art will appreciate that it is advantageous to minimize the size of the surgical incision. Currently, the incision necessary for the insertion of a soft IOL may be in a range up to approximately 3.2-4.1 mm. A smaller incision reduces trauma to the eye and may speed healing and may reduce any surgically-related optical effects. However, as the size of the incision is decreased, there will arise a need to more compactly deliver lenses, particularly to avoid damage to the IOL during insertion through the smaller incision.

Further, insertion of a lens through the incision in the eye during a surgical procedure may cause post-operative inflammation, increased intraocular pressure, and/or posterior and anterior capsular opacification (PCO and ACO), and, for example, and these effects must be accounted for by the surgeon, both during and following surgery. If not accounted for, these effects may cause the onset of detrimental side effects, or may cause a failure to correct vision.

Thus, an implanted optic may be damaged upon insertion into the eye, and/or may cause temporary or permanent damage to the eye due to the insertion, thereby adversely affecting optical performance and/or cosmetic appearance. Likewise, surgical side effects that may cause such temporary damage from the insertion must be treated or prevented, preferably without further damage to the lens or the eye, or performance of the implanted optic may be adversely affected.

A need therefore exists to protect an implantable lens, such as an intraocular lens, comprised of a soft optic material, during insertion, and/or to negate the adverse side effects of implantation of a lens.

SUMMARY OF THE INVENTION

An apparatus, system and method for coating an implantable lens for implantation, wherein the lens includes at least an optic, is disclosed. The apparatus, system and method may include at least one coating layer applied to at least one surface of the optic, wherein the coating layer may at least partially protect the optic during the implantation, and wherein the coating layer may be removable following implantation. The coating layer may include a protectant, a lubricant and/or medication, and may be in the form of a biodegradable polymer and/or a film.

The apparatus, system and method may, more specifically, be for coating an intraocular lens. Such an apparatus, system and method for coating and/or protecting an intraocular lens may include a means physically associated with the intraocular lens for protecting the lens at the implantation and a means for removing the protective means upon the implantation. The means for removal may include, for example, a tab. The tab may be sized to accommodate a surgical tool for the implantation. The tab may include one or more features that aid in removal of the protective means. Such features may include one of color and texture.

The apparatus, system and method may also include maintaining characteristics of an intraocular lens. For example, the method of maintaining characteristics of an intraocular lens may include coating the intraocular lens with a protective coating and/or a medicinal coating prior to implantation, enabling the implantation of the intraocular lens, and removing at least one of the protective coating and/or the medicinal coating after the implantation.

An intraocular lens suitable for implanting into an eye is also disclosed. The lens may include an optic for improving the vision of the eye, and a haptic for supporting the optic within the capsular bag of the eye. At least one of the optic and the haptic may include at least one coating layer, wherein the at least one coating layer may at least partially protect the at least one of the optic and the haptic at least during the implantation. In an embodiment, the at least one coating layer is removable following implantation. The coating layer may additionally provide medication.

The medication is on the at least one surface of the coating layer proximate to the optic. The medication may comprise a treatment, such as for reducing intraocular pressure. The medication may be, for example, a steroid. The medication may, for example, be activated by the implantation.

Thus, the present invention protects an implantable lens during insertion, and/or negates the adverse side effects of implantation of a lens, such as an intraocular lens.

BRIEF DESCRIPTION OF THE FIGURES

Understanding of the present invention will be facilitated by consideration of the following detailed description of the preferred embodiments of the present invention taken in conjunction with the accompanying drawings, in which like numerals refer to like parts.

DETAILED DESCRIPTION OF THE PREFERRED EMBODIMENTS

It is to be understood that the figures and descriptions of the present invention have been simplified to illustrate elements that are relevant for a clear understanding of the present invention, while eliminating, for the purpose of clarity, many other elements found in typical lenses, lens systems and methods, and in protective coatings and techniques. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

The present invention provides protection for the characteristics of implantable lenses, and may further provide positive benefits to negate side effects often associated with a surgical insertion of an implantable lens. In particular, the present invention may include coating or treating the surface(s), such as the anterior, posterior, or both, of any implantable IOL. Such a coating or treatment may be temporary in nature. The coating or treatment may be protective, and/or may be impregnated with secondary materials, such as medicinal materials, to combat or reduce side effects known to exist from surgery to the eye.

The present invention may additionally include an inert, removable film on an implantable optic, separate from, integral with, or equivalent to the aforementioned coating. The film may provide protection and/or structural support during insertion. The film may be removed late in the surgical process, such as after or simultaneously with implementation in vivo.

Additionally, the present invention may include a protective and/or medicinal coating on the surgical insertion tools employed during an implantation of, for example, an IOL, to effectively protect the optic and/or to protect from side effects of implantation of the optic. A coating or protective layer on a surgical tool may not require removal after the procedure is complete, unlike a coating or layer on the optic.

The present invention may be utilized on any type of lens and/or lens system that may cause harm, adverse effects, or that may suffer from adverse performance due to the adverse effects or based on damage during insertion, in the eye, for example. Such lens systems include single lens designs including but not limited to monofocal, multifocal, toric, accommodating IOLs, next generation designs for accommodating IOLs, and dual optic lenses, by way of non-limiting example.

Figure 1:
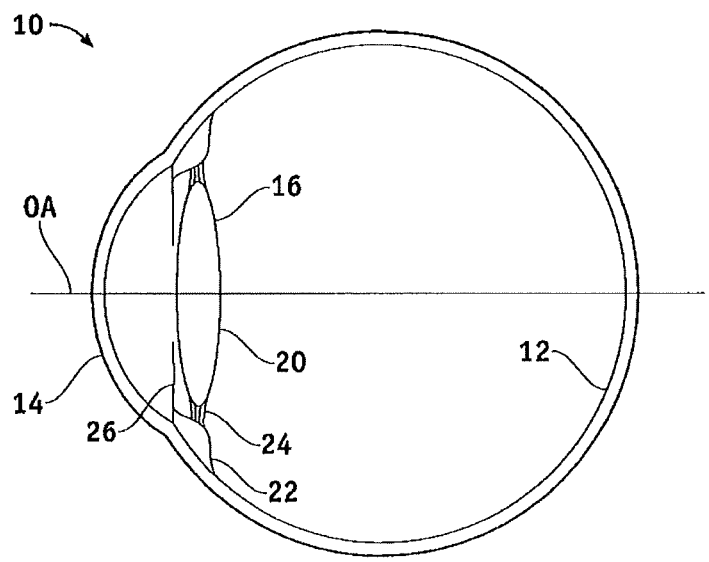
FIG. 1 illustrates a diagram of the eye.

FIG. 1 is a diagram of an eye. Eye 10 includes retina 12 for receiving an image produced by cornea 14 and natural lens 16 from light incident upon eye 10. Natural lens 16 is disposed within capsular bag 20, which separates anterior and posterior chambers of eye 10. Capsular bag 20 is a resilient material that changes the shape and/or location of natural lens 16 in response to ocular forces produced when ciliary muscles 22 contract and stretch natural lens 16 via zonules 24 disposed about an equatorial region of capsular bag 20.

This shape change effectuated by ciliary muscles 22 may flatten natural lens 16, thereby producing a relatively low optical power for providing distant vision in an emmetropic eye. To produce intermediate and/or near vision, ciliary muscles 22 relax, thereby relieving tension on zonules 24.

The resiliency of capsular bag 20 thus provides an ocular force to modify the curvature of natural lens 16, to thereby provide an optical power suitable for required vision. This modification, or "accommodation," allows for changes the focus of the eye for different viewing distances.

Eye 10 also includes iris 26. Iris 26 may operate to change the aperture size of eye 10. More specifically, the diameter of the incoming light beam is controlled by iris 26, which forms the aperture stop of eye 10.

Figure 2:
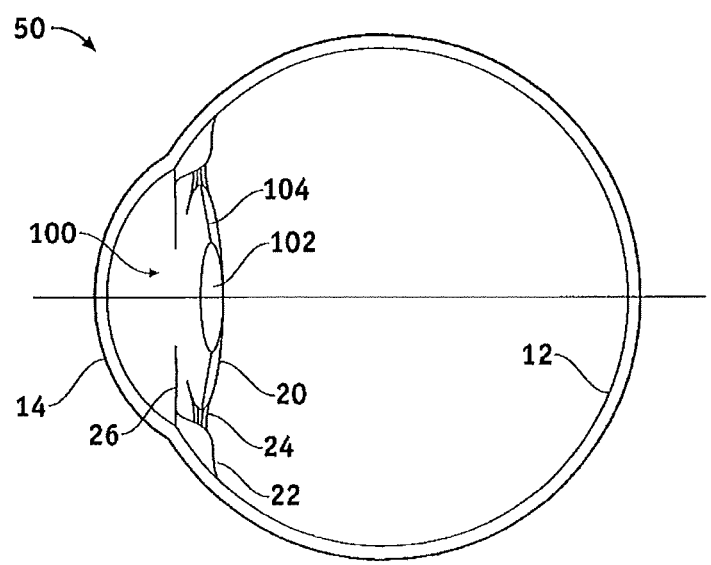
FIG. 2 illustrates a diagram of an eye with an implanted IOL.

Referring now to FIG. 2, there is shown an eye 10 having a lens (natural lens 16 of FIG. 1) replaced with an IOL 100. Natural lens 16 may require removal due to a refractive lens exchange, or due to a disease such as cataracts, for example. Once removed, natural lens 16 may then be replaced by IOL 100 to provide improved vision in eye 10. Eye 10 may include IOL 100 with optic 102, cornea 14, retina 12, haptics or support structure 104 for centering optic 102, and, in the case of an accommodating IOL (aIOL), haptics 104 for transferring ocular forces from ciliary muscle 22, zonules 24, and/or capsular bag 20 to optic 102 to change its shape, power, and/or axial location relative to retina 12.

Removal of natural lens 16 may occur during a surgical procedure. The surgery typically includes a very small, self sealing incision in the eye to permit insertion and removal of an IOL 100 and tools. More specifically, IOL 100 is typically inserted through an incision less than 4.5 mm, and preferably less than 2.5 mm, made in the eye 10 during the surgical procedure.

Various techniques may be employed for implanting IOL 100 through the surgical incision and into eye 10. A physician may, for example, access the anterior aspect of the capsular bag 20 via an appropriate technique. The physician may then incise the anterior of the bag 20, such as by making a circular opening, or the physician may make a dumbbell shaped incision by forming two small circular openings and connecting them with a third straight line incision. The natural lens 16 may then be removed from the capsular bag by any of variety of techniques, such as phacoemulsification, cryogenic and/or radiative methods.

In phacoemulsification, for example, an irrigation-aspiration instrument having an ultrasonic vibration is inserted through the incision to gently break up natural lens 16 and aspirate it out in tiny pieces in order to make way for the placement of IOL 100. The tip of this instrument vibrates at ultrasonic frequency to sculpt and emulsify the lens, while a pump aspirates particles through the tip. To inhibit further cell growth, often the physician may polish the capsular bag to remove or kill remaining lens epithelial cells. Other treatments, such as cryogenically and/or through radiative techniques, via anti-metabolites, or via chemical and osmotic agents, for example, have been attempted to remove or kill remaining cells.

IOL 100 may be surgically implanted into capsular bag 20 following removal of natural lens 16, in addition to natural lens 16, or to replace a lens that has previously replaced natural lens 16. In order to implant IOL 100, the incision may be enlarged, or IOL 100 may be folded, or otherwise distorted to fit through the incision, for example. To fold IOL 100, a holder/folder, or an insertion device, such as a catheter, for example, may be used.

IOL 100 may be inserted in the posterior chamber in capsular bag 20. If IOL 100 comprises separate anterior and posterior portions, the physician may fold or roll the posterior portion, and may place it in the capsular bag through the anterior opening after allowing the posterior portion to unroll/unfold. The physician may then manipulate IOL 100, using surgical tools, to adjust the positioning of the posterior portion until it is within satisfactory limits. Next, the physician may roll/fold and implant the anterior portion, and may align and assemble the anterior portion to the posterior portion as needed.

This rolling/folding, implantation, unrolling/folding and alignment/assembly may be repeated until the lens system associated with IOL 100 is inside the capsular bag. Because a smaller incision is required to engage in the surgical insertion of folded lens elements, as discussed immediately hereinabove, fewer or no stitches may be needed and the patient's recovery time may be appreciably shorter when using a foldable IOL. However, in such cases, significant manipulation of the IOL 100 may be required, as discussed above.

It is contemplated that conventional IOL folding devices, injectors, syringes and or shooters may be used to manipulate and/or insert the exemplary lens systems through or within the surgical incision, as described herein. It is further contemplated that, upon folding/rolling, the lens system may be placed in an insertion tool, and/or may be inserted into the eye via an insertion tool. Finally, the lens system may be adjusted by a physician during implantation, and/or may be temporarily held in place in the eye by the use of dissolvable sutures, or a detachable or dissolvable clip, for example.

An exemplary insertion tool employs a hollow insertion tube having a diameter that permits the folded IOL to pass through the hollow space defined by the tube without permanent deformation, and a plunger assembly including a rod, often made of metal, which is moved longitudinally in the hollow space, in contact with optic 102 of IOL 100, to thereby push IOL 100 through the hollow space. Several disadvantages are apparent in such insertion tools. For example, pushing, without trapping or holding, IOL 100 through and out of the hollow space defined by the tube may cause IOL 100 to be released from the insertion device without precise control, so that the released IOL may damage eye 10, may itself be damaged, and/or may be mispositioned in eye 10. More particularly, the rod may mark the surface of optic 102 and/or tear optic 102, particularly when optic 102 is made of soft materials, such as soft elastomeric silicone polymeric materials.

Of note, each of the insertion tools, adjustment techniques and techniques for holding in place IOL 100 may result in damage to optic 102, or eye 10. This damage may adversely affect eye 10, and/or affect the performance of optic 102.

A number of different lens systems may be implanted to provide optic 102 via the surgical implantation techniques discussed hereinabove. It is preferable to avoid damage to the lens during implantation, adjustment or holding in place of the lens, via insertion tools, and to avoid abrasion from the sidewalls of the incision, the physician, or the dissolvable clip, and to avoid side effects following implantation, when surgically implanting such lenses. In particular, lens systems including single lenses, accommodating IOLs, next generation lenses for aIOLs, and dual optic lenses, by way of non-limiting example, may benefit from the protective embodiments discussed herein.

A single lens system, such as a single, fixed class IOL, has a single fixed focal length, or an equivalent single fixed power. Unlike the eye's natural lens, which may adjust its focal length and/or axial location within a particular range by accommodation, single focal length IOLs generally do not accommodate. As a result, distant objects may appear in focus, while objects at closer distances appear blurred.

On the other hand, an aIOL may move axially and/or adjust optical power within a particular range. As a result, an eye with an aIOL may clearly focus on objects at a range of distances from the eye. This ability to accommodate is of large benefit to the patient, and more closely approximates the patient's natural vision than does a single focal length IOL.

Figure 3:
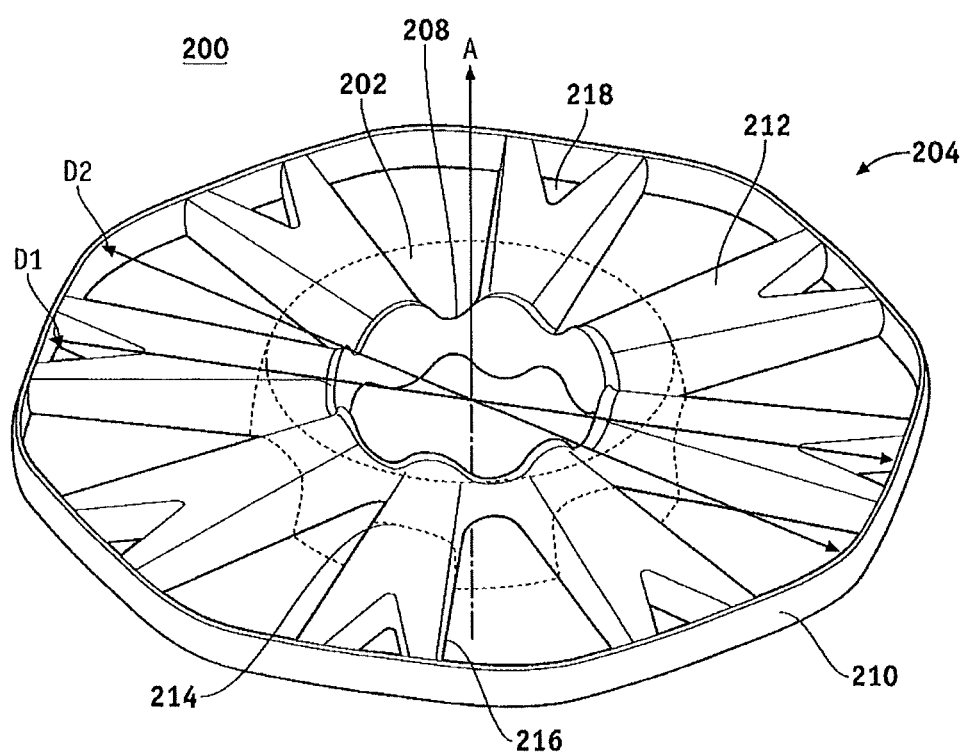
FIG. 3 illustrates an IOL according to an embodiment of the present invention.

Referring now to FIG. 3, an exemplary lens system comprising aIOL 200 is shown disposed about optical axis A. Accommodating IOL 200 includes optic 202, and haptic 204 configured to effectively transfer an ocular force from an eye to optic 202 so as to produce a range of powers in response to the ocular force. Haptic 204 includes inner structure 208 and outer structure 210, and plurality of arms 212 connecting coupling structures 208, 210 to one another to efficiently and effectively transfer ocular forces. Haptic 204 thus changes the shape and/or axial location of optic 202, thereby providing a change in optic power and/or focal plane location of optic 202. Arms 212 each include proximal end 214 coupled to inner structure 208, and distal end 216 coupled to outer structure 210.

Optic 202 may be formed directly onto haptic 204. Alternatively, optic 202 may be fabricated separately from haptic 204, and attached to haptic 204. In certain embodiments, haptic 204 may be machined or molded, and optic 202 may be molded and/or machined over, into or on top of haptic 204.

Optic 202 may be a relatively soft material, so that optic 202 may deform or change shape readily under the limited deforming forces produced by capsular bag 20 and/or ciliary muscle 22. An exemplary material for optic 202 is a relatively soft silicone material, although other suitable materials may be used as will be understood to those skilled in the art. The stiffness of optic 202 may be in the range of approximately 0.5 to 500 kPa, for example. In more particular exemplary embodiments, the stiffness of optic may be in the range of approximately 25 and 200 kPa, or more specifically in the range of 25 and 80 kPa, for example.

In contrast with optic 202, at least portions of haptic 204, such as arms 212, may generally be of a relatively stiffer material than that of optic 202, so that haptic 204 may efficiently transmit ocular forces to optic 202. An exemplary material for haptic 204 is a relatively stiff silicone material, although other suitable materials may be used, such as acrylic, polystyrene, polymethyl methacrylate, or clear polyurethanes. The stiffness of haptic 204 may be greater than or equal to 500 kPa, or, in a more particular exemplary embodiment, may be greater than or equal to 3000 kPa, for example.

Arms 212 may extend into optic 202, and may include the clear aperture of optic 202. As used herein, the term "clear aperture" means the area of the optic that restricts the extent of rays from a collimated source or a distant light source that can be imaged by the optic. The clear aperture is usually circular, and may be specified by its diameter. In some embodiments, the clear aperture may have the same or substantially the same diameter as optic 202. Alternatively, the diameter of the clear aperture may be smaller than the diameter of optic 202, for example, due to the presence of a glare or PCO reducing structure disposed about a peripheral region of optic 202.

Since inner structure 208 and proximal ends 214 of arms 212 may be located inside optic 202 and within the clear aperture of optic 202, at least these portions of haptic 204 may be beneficially transparent or nearly transparent, so as to not substantially block or scatter light transmitted through optic 202. In addition, these portions of haptic 204 may have a refractive index that matches the refractive index of optic 202, so that interfaces between optic 202 and haptic 204 do not produce significant reflections or refractions that might produce scattered light within the eye, which scattered light might appear as a glare or haze.

By way of example, for a planar surface at normal incidence between air (a refractive index of 1) and glass (a refractive index of 1.5), 4% of the incident power is reflected at the interface. If, instead of relative refractive indices of 1 and 1.5, the refractive indices differ by 4% or less, such as the difference between 1.5 and 1.56, or 1.5 and 1.44, for example, reflection is reduced to 0.04%, which is a factor of 100 improvement over the air-glass interface. Finally, if the relative refractive indices differ by only 0.3%, reflection is reduced to 0.00028%. The above base value of a refractive index of 1.5 was chosen for simplicity of illustration, and each of haptic 204 and optic 202 may have any suitable refractive index, as will be understood to those skilled in the art.

Thus, the refractive indices of optic 202 and at least portions of haptic 204 are preferably equal, or substantially equal, in order to minimize the reflection discussed above. Note that haptic 204 and optic 202 may optionally have different dispersions, wherein the refractive index variation, as a function of wavelength, may be different for haptic 204 and optic 202.

Returning now more particularly to FIG. 3, the extension of arms 212 into optic 202 generally allows more effective transfer of radial forces along arms 212 to optic 202, since the inner diameter of inner structure 208 is less than the outer diameter of optic 202. This relatively small "active area" of optic 202, located inside inner structure 208, allows ocular forces to be distributed over a smaller peripheral zone about the active area than if the same force were distributed over a periphery of the outer diameter of optic 202. Since ocular forces are thus effectively concentrated over a relatively small area, the pressure near the center of optic 202 is increased, which in turn increases the amount of curvature change, and thus optical power change, induced for a given amount of radial force on outer structure 210 and arms 212. As a result, the limited ciliary muscle or capsular bag force may produce a greater accommodative power change, i.e., axial translation, of optic 202. However, avoidance of modification, distortion, or similar damage to at least the active area during insertion of IOL 200 is thus necessitated for proper performance of optic 202.

The inner diameter of inner structure 208 is generally selected to be at least large enough for the active area of optic 202 to provide a change in optical power under scotopic lighting conditions, such as with a pupil diameter of the eye of 2 to 3 mm, for example. For example, when IOL 200 is used in the human eye, the active area is generally sufficiently large if the inner diameter of inner surface 208 is between 2 and 4 mm, or between 2.5 and 3.5 mm, or 3 mm+/−0.25 mm, for example.

In some embodiments, the axial thickness of inner structure 208 between arms 212, and/or overlapping proximal ends 214, is relatively large, for example, to help distribute more radial force on outer structure 210 to change the shape of the anterior and posterior surfaces of optic 202. The ratio of the optic center thickness to the axial thickness of inner structure 208 may be less than or equal to 2, for example. Greater accommodative power change in optic 202 may be provided when the ratio of the optic center thickness to the axial thickness of inner structure 208 is less than 1.8, or more specifically less than 1.5, for example. Areas of greater thickness may, as will be understood in light of the disclosure herein, necessitate less protection by, for example, the coating and/or film discussed herein throughout, in order to avoid damage during insertion, for example.

Inner structure 208 may be a continuous ring and may generally have a radial thickness that is from 0.1 to 0.2 mm, or specifically about 0.15 mm+/−0.03 mm, for example. While the continuous ring form of inner structure 208 may maintain the form of optic 202 upon deformation during accommodation, a relatively small radial thickness of inner structure 208 may reduce the stiffness of inner structure 208 so that a greater percentage of the radial forces transferred from arms 212 are focused on changing the shape, and thus the accommodative optical power, of optic 202.

Outer structure 210 may be broken at predetermined locations. Arms 212 may be bifurcated or split at distal ends 216 to form openings 218. Of course, in light of the discussion herein of relative indices of refraction, it may also be preferable to protect arms 212 during insertion of 200, such as to maintain a designed-for relative refractive index and to prevent damage that may cause unwanted reflections, for example. Openings 218 may have a triangular shape, as shown in the illustrated embodiment. Alternatively, openings 218 may have other shapes, such as an oval-shape, for example. Openings 218 may be configured to reduce the mass of haptic 204, to help direct radial forces towards inner structure 208, and/or to control the shape of outer structure 210 during accommodation, such as to avoid bending or buckling, for example.

Figure 4:
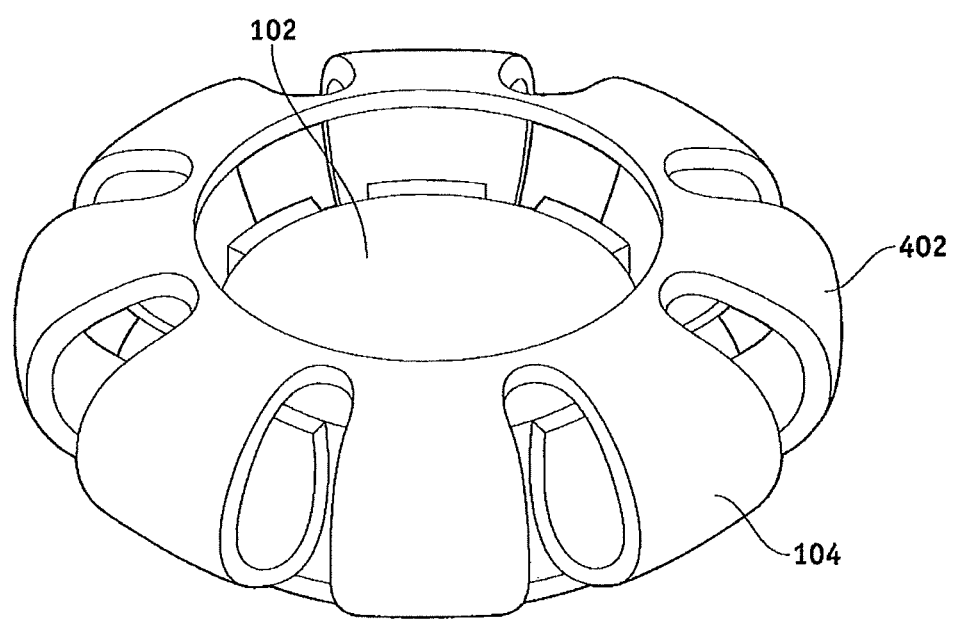
FIG. 4 illustrates an exemplary optic for use in the present invention.

Another exemplary optic for use in the present invention is shown in FIG. 4. FIG. 4 shows a deformable optic 102 with an exemplary haptic 104, shown in isometric view and removed from the eye. The view of FIG. 4 shows that haptic 104 extends a full 360° azimuthally around the edge of optic 102.

The exemplary haptic 104 of FIG. 4 has various segments 402, or filaments, each of which extends generally in a plane parallel to the optical axis of the IOL 100. For the exemplary haptic 104 of FIG. 4, segments 402 are joined to each other at one end, extend radially outward to contact the capsular bag, and extend radially inward to contact the edge of optic 102. At the edge of optic 102, the haptic segments 402 may remain separate from each other, as shown in FIG. 4, or alternatively some or all segments may be joined together. Any or all of the width, shape and thickness of the segments may optionally vary along the length of the segments. The haptic may have any suitable number of segments, including but not limited 2, 4, 6, 8, 10, 12, 14, and 16 segments.

As shown, the region of contact between optic 102 and haptic 104 in FIG. 4 may extend into the edge of optic 102, in a manner similar to the interface between a bicycle tire and a rim that holds the tire in place. An exemplary region of contact between haptic 104 and optic 102 is described and shown in greater detail in United States Patent Publication 2008/0161913, the entire disclosure of which is incorporated herein by reference as if set forth in its entirety.

Figure 5:
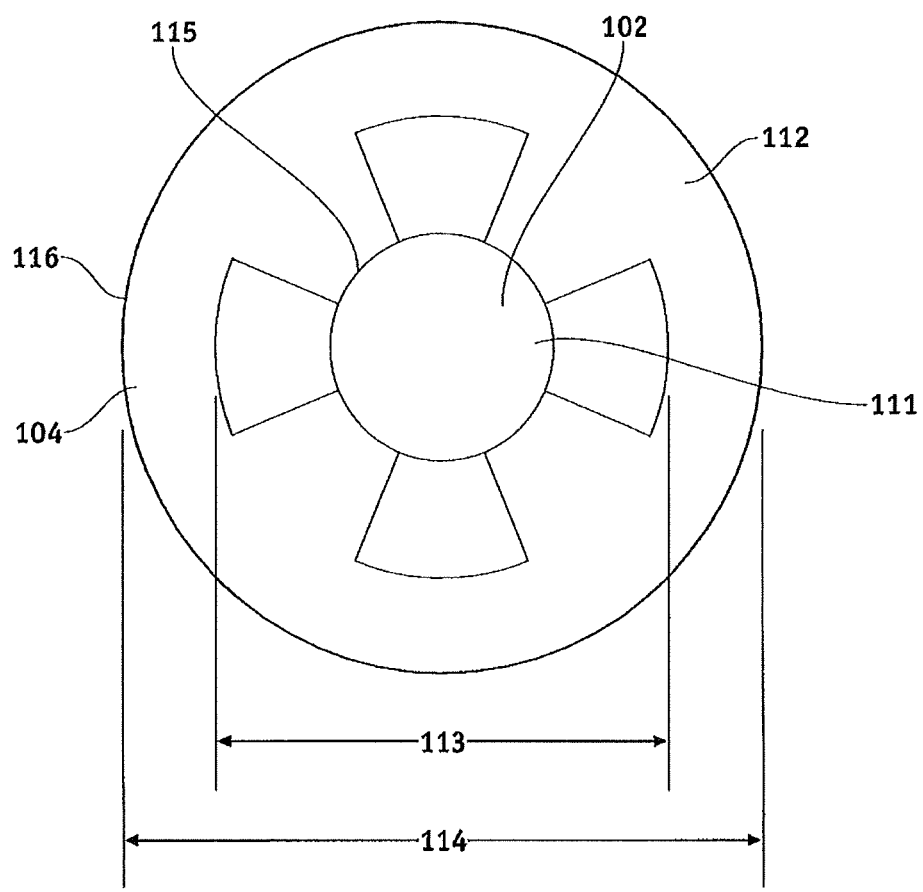
FIG. 5 illustrates an exemplary haptic and optic for use in the present invention.

Another exemplary haptic 104 and optic 102 is shown in the isometric illustration of FIG. 5. Exemplary haptic 104 has various segments or filaments, each of which extends generally radially in a plane roughly perpendicular to the optical axis of the IOL 100. For the exemplary haptic 104 of FIG. 5, segments 402 may be joined to each other at the outer circumference and extend radially inward to contact the edge of optic 102. Alternatively, segments 402 need not be joined together at the outer circumference. At locations other than the outer circumference, haptic segments 402 may remain separate from each other, as shown in FIG. 5, or alternatively some or all segments may be joined together.

The exemplary haptic 104 is then compressed radially, so that the overall diameter of haptic 104 is reduced. A typical compression may be on the order of about 1 mm, although more or less compression may be used. For instance, haptic 104 may be compressed by a fraction of its diameter, such as a value in the range of about 0.4% to about 2.0% compression.

Haptic 104 may engage a portion of the periphery of optic 102 in a region roughly around equator 115 of optic 102. This exemplary haptic 104 contacts optic 102 in four regions, each roughly equally spaced apart around equator 115 of optic 102, although any suitable number of contact portions may be used and these portions need not be spaced equally apart. Haptic 104 includes a ring, also known as a circumferential ring. The ring has an inner diameter given by element 113, and an outer diameter given by element 114. The ratio of inner to outer diameters may vary as a function of the stiffness of haptic 104.

For haptic 104 in FIG. 5, the outer diameter 116 of the ring is the outer portion of haptic 104, and the outer portion of haptic 104 may remain in contact with the capsular bag of the eye during and after implantation, and such a configuration may be typical for embodiments of haptic 104, certain of which exemplary embodiments are discussed herein.

Alternatively, the annular ring may be contained in the interior of haptic 104, with arms or filaments that may extend outward beyond the outer diameter of the ring to contact the capsular bag. As a further alternative, the inner diameter of the ring may be the inner diameter of haptic 104, and may contact the circumference or the equator of optic 102. Such a region of contact between haptic 104 and optic 102 is described and shown in greater detail in United States Patent Publication 2008/0161914, the entire disclosure of which is incorporated herein by reference as if set forth in its entirety.

Figure 6:
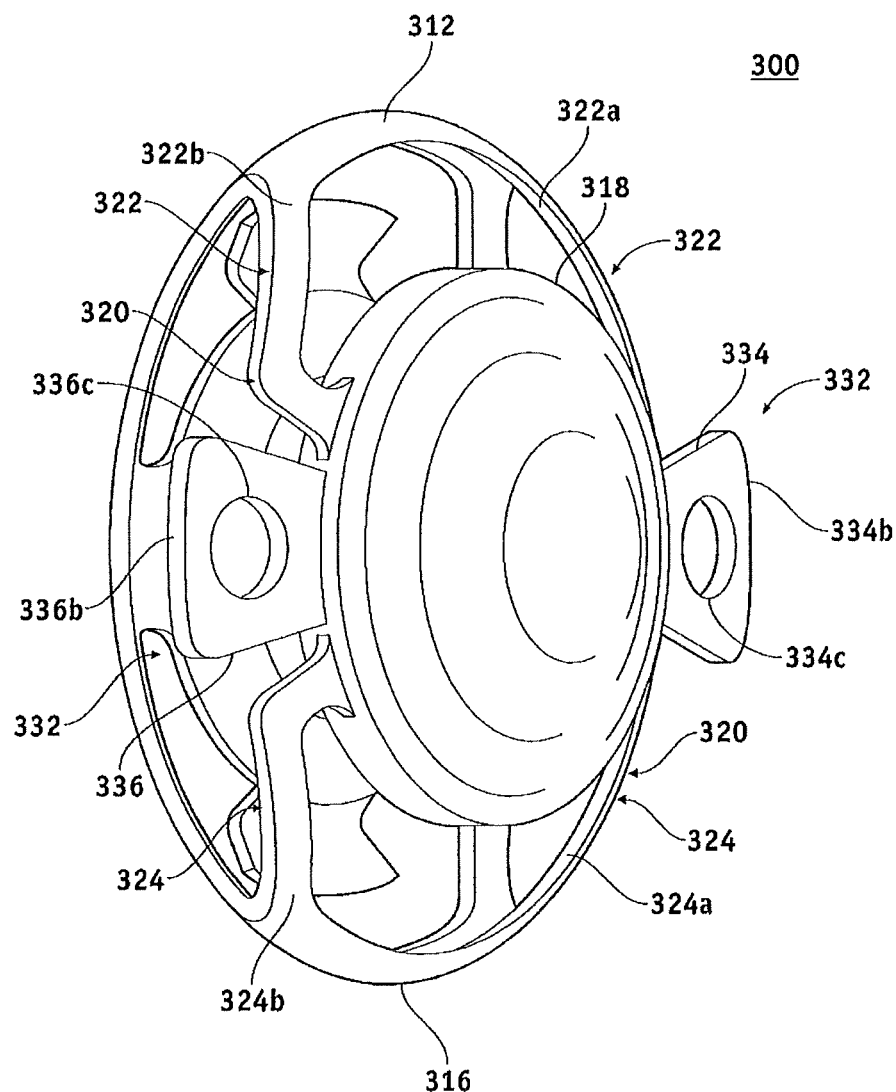
FIG. 6 illustrates an exemplary dual optic lens for use in the present invention.

An exemplary dual optic lens in accordance with the present invention is shown in FIG. 6. FIG. 6 illustrates a rear perspective of the exemplary dual optic lens. As illustrated, the posterior portion of lens 300 includes posterior viewing element 318 and posterior biasing element 320. Posterior biasing element 320 includes a first posterior translation member 322 extending from the posterior viewing element 318 to the first apex 312, and second posterior translation member 324 extending from posterior viewing element 318 to second apex 316. In the illustrated embodiment, the first posterior translation member comprises right arm 322a and left arm 322b. Likewise, the depicted second posterior translation member 324 comprises right arm 324a and left arm 324b. However, either or both of the first and second posterior translation members 322, 324 may comprise a single arm or member, or more than two arms or members.

Anterior biasing element 308 and posterior biasing element may be configured symmetrically. As used herein with respect to biasing elements 308, 320, "symmetric" or "symmetrically" means that, as the lens system 300 is viewed from the side, first anterior translation member 310 and first posterior translation member 322 extend from first apex 312 at substantially equal first anterior and posterior biasing angles $\theta_1, \theta_2$ with respect to the edge of a plane which is substantially orthogonal to the optical axis and intersects first and second apexes 312, 316, and/or that the second anterior translation member 314 and the second posterior translation member 324 extend from the second apex 316 at substantially equal second anterior and posterior biasing angles $\theta_3, \theta_4$ with respect to the same plane. Alternative or asymmetric configurations of biasing elements are, of course, possible.

Both anterior viewing element 306 and posterior viewing element 318 may comprise optic 102 having refractive (and diffractive) power. In alternative embodiments, one or both of anterior and posterior viewing elements 306, 318 may comprise optic 102 with a surrounding or partially surrounding perimeter members. In still further variations, one of viewing elements 306, 318 may comprise a zero-power lens or a transparent member.

Retention portion 326 may be coupled to anterior portion 302, preferably at anterior viewing element 306. Retention portion 326 may include first retention member 328 and second retention member 330, although in alternative embodiments retention portion 326 may be omitted altogether, or may comprise only one retention member or more than two retention members.

Posterior portion 304 may include distending portion 332, attached to posterior viewing element 318. Distending portion 332 may include first distending member 334, which in turn may include fixed end 334a, free end 334b opposite fixed end 334a and opening 334c. Distending portion 332 also comprises second distending member 336 with fixed end 336a, free end 336b and opening 336c. Distending portion 332 may be omitted altogether, or may comprise a single distending member or more than two distending members.

Anterior and posterior biasing elements 308, 320 may function in a springlike manner to permit anterior viewing element 306 and posterior viewing element 318 to move relative to each other generally along the optical axis. Biasing elements 308, 320 bias the viewing elements 306, 318 apart so that elements 306, 308 separate to the accommodated state shown in FIG. 6. Thus, in the absence of any external forces, the viewing elements are at their maximum separation along the optical axis. Viewing elements 306, 318 of lens system 300 may be moved toward each other, such as in response to a ciliary muscle force of up to 2 grams, to provide an unaccommodated position by applying appropriate forces upon anterior and posterior portions 302, 304 and/or apices 312, 316.

When the lens system 300 is implanted in capsular bag 20, the above described biasing forces cause lens system 300 to expand along the optical axis so as to interact with both the posterior and anterior aspects of capsular bag 20. Such interaction occurs throughout the entire range of motion of ciliary muscle 22. At one extreme, ciliary muscle 22 may relax and zonules 24 pull capsular bag 20 radially so as to cause bag 20 to become more disk shaped. The anterior and posterior sides of bag 20, in turn, apply force to anterior and posterior portions 302, 304, thereby forcing viewing elements 306, 318 of optic 102 toward each other into the accommodated position. At the other extreme, ciliary muscle 22 may contract and zonules 24 move inwardly to provide slack in capsular bag 20 and allow bag 20 to become more football-shaped. The slack in bag 20 may be taken up due to the biasing-apart of anterior and posterior viewing elements 306, 318. As the radial tension in bag 20 is reduced, viewing elements 306, 318 move away from each other into an accommodated position. As the distance between anterior and posterior viewing elements 306, 318 is varied, the focal length of the lens system 300 changes accordingly. Such an optic is described and shown in greater detail in United States Patent Publication 2006/0259139, and U.S. Pat. No. 7,118,596, the entire disclosures of which are incorporated herein by reference as if set forth in the entirety.

However, damage to optic 102, such as during implantation, or adverse effects caused by implantation to capsular bag 20, ciliary muscle 22, and/or zonules 24 may negate the anticipated accommodation and/or optical properties of the implanted lens. Further, because each of the aforementioned lens systems may, as discussed, be implanted via the surgical techniques discussed, each such lens or lens system may, upon implantation, suffer from the aforementioned issues associated with surgical insertion, namely damage to one or more of the referenced aspects of optic 102 during implantation, damage to one or more aspects of haptic 104 during implantation, or swelling, infection, or similar adverse side effects, such as to capsular bag 20 and/or ciliary muscle 22, that may cause underperformance of the implanted lens system.

Figure 7:
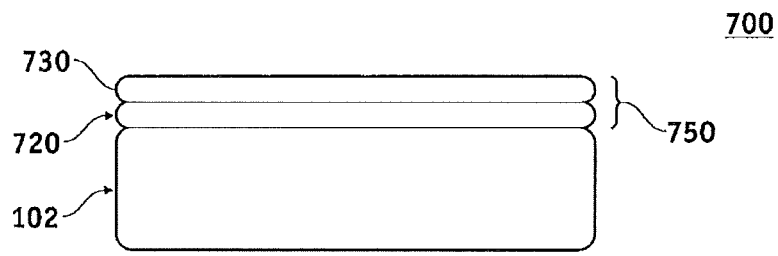
FIG. 7 illustrates a coating formed on an optic of the type discussed with respect to FIGS. 3-6.

Referring now to FIG. 7, there is shown a coating formed on optic 102 of the type discussed in the exemplary embodiments of FIGS. 3-6 to ameliorate certain of the surgical issues discussed, according to an aspect of the present invention. As illustrated, optical assembly 700 may include optic 102, such as those optics described hereinabove, and coating 750. Coating 750 may include any number of layers, such as one, two, three, five, or more layers. One or more of the layers may vary in thickness, such as to differentially protect various portions of optic 102 and/or haptic 104 that are of varied thickness, as referenced above with respect to FIG. 3. Coating 750, as shown in the exemplary embodiment of FIG. 7, may include first layer 720 and second layer 730 for coating the anterior surface of optic 102. According to an embodiment, an IOL may have multiple coating layers and after implantation into to an eye, one or more layers may be removed leaving one or more layers on the IOL either permanently, temporarily for degradation, or a combination thereof.

Figure 8:
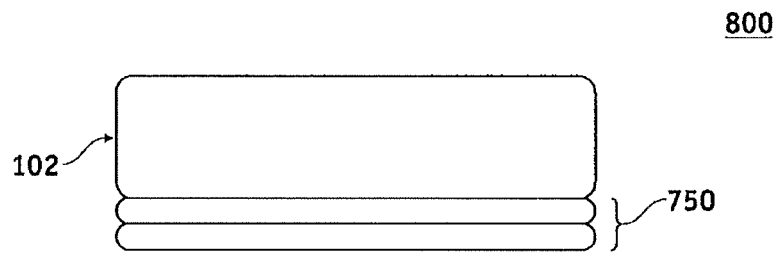
FIG. 8 illustrates a coating formed on an optic according to an aspect of the present invention.

Referring now additionally to FIG. 8, there shown a coating 750 formed on optic 102. Coating 750 on optic 102 may be on the anterior of the optic (shown in FIG. 7), posterior of the optic (shown in FIG. 8), or on both surfaces of the optic. Coating 750 may be a film deposition of a permanent or temporary material. A temporary material may degrade away, dissolve, or the like, in some defined period of time under in-use conditions, such as in less than six weeks, less than two weeks, less than one week, in a few days and/or in a few hours, for example. Degradation may occur over a predefined time period, from as little as minute to as long as three years depending upon the design of the film, the chemical properties of the film, the medicinal attributes of the film, the purpose of the film, patient healing time, physician preferences, industry standards, and/or the like. Different layers of coating 750 may degrade over different time periods, such as to provide timed release of different medicines impregnated within coating 750, such as steroidals, anti-infectants, or the like, which medicines may be differently provided within each of the multiple layers for release at different times upon degradation or dissolution of the above layer, for example.

Coating 750 may include areas of variable thickness in order to target greater or lesser protection, or of different time release aspects, to different areas of the lens, as referenced hereinabove. For example, such a variable thickness in coating 750 may for targeting the features of coating 750, such as the medicinal features discussed above, to select portions of optic 102, of haptic 104 or of the eye in order to optimize the benefits provided by those features.

Coating 750 may be inert or active. An inert coating may take the form of a coating that is not chemically reactive. An inert coating may also be conditionally inert. For example, coating 750 may be inert under ordinary conditions, but may become reactive under certain conditions, such as under high pressure, high temperature, or in the presence of a catalyst, for example.

An active coating may include an active material, such as the medicinal material described hereinabove. An active coating may provide implantation enhancements, such as an optically active additive to be activated upon implantation of optic 102 into the eye, or the like. Thus, the optically active additive may include an organic or inorganic material which, when added to coating 750, makes coating 750 reactive to certain catalysts, such as ultra violet light or colored light, for example. Such additive may prove useful in inspection of optic 102 before or during implantation, or to ensure that coating 750 has been completely removed or completely dissolved, for example.

Coating 750 may be applied, such as via adhesion, impregnation, contact force association, or the like, to optic 102, haptic 104, or both optic 102 and haptic 104. Further, the constituents of coating 750 may be different over optic 102 and haptic 104, such as due to the different properties, thicknesses, or mechanical features of optic 102 and haptic 104. Similarly, the constituents or thickness or number of layers of coating 750 may vary as between, or within, optic 102 and/or haptic 104. For example, because haptic 104 may be mechanically less pliable than optic 102, haptic 104 may have coating 750 of high lubricity, such as in order to aid in passing the lens, and particularly the stiff haptic 104, through an injection tool. Moreover, in this exemplary embodiment, coating 750 on optic 102 may not be high in lubricity, but rather may be thicker and multilayered, such as in order to better protect the more delicate nature of optic 102, and/or to deliver medication via one of the layers of coating 750 upon optic 102.

Coating 750 may protect optic 102, and/or haptic 104, and ideally may not degrade optic 710. Coating 750 may, for example, address degradation from the folding/unfolding issues associated with the insertion process, as discussed with respect to FIG. 2, such as by providing lubrication to aid in the folding/unfolding. Further, coating 750 may aid the delivery of optic 102 through an insertion tool, such as by providing lubricity as needed, and/or by reducing friction and tackiness, for example.

Coating 750 may be a thin film, such as to preclude coating 750 from substantially affecting the optical properties of the IOL prior to dissolving completely, for example. The thickness of the film may be on the order of 1-50 nm, in the range of 1-50 microns, or in the range of 1 to 5 angstroms, for example. Coating 750 may include layer(s) selected from a class of materials that include biodegradable polymers, such as polylactic acid and poly-glycolic acid, for example. As used herein, biodegradable polymers include all polymers and like materials that are biocompatible and that may degrade or dissolve in a predetermined amount of time, such as from days to years, for example. Biodegradable polymers may be impregnated with the aforementioned medicinal substance, such as a steroid, to treat post operative inflammation, or to reduce or prevent anterior capsular opacification/posterior capsule opacification, or to reduce intra-ocular pressures, for example.

The film may include a color or texture to aid in the removal of coating 750 from the lens. Further, because the thin film may adhere to the lens via surface tension, adhesion, or other physical forces during the insertion process, certain steps for removal of the thin film may be performed. For example, irrigation after phacoemulsification may lift coating 750 from optic 102, because silicone is less tacky when wet. Additionally or alternatively, visco-elastic features may be included in coating 750 to create pressure differences to lift coating 750. Such a visco-elastic feature may include any dispersive or cohesive elements in coating 750 to aid removal.

Coating 750 may be an opaque film, such as to aid in the insertion process. For example, coating 750 may provide a doctor a visual cue to aid in the insertion process, and/or to aid in the removal of coating 750. An opaque coating 750 may, in exemplary embodiments, dissolve, or be otherwise removed, before use of the lens, in part because such opacity may prohibit vision through the lens.

Figure 9:
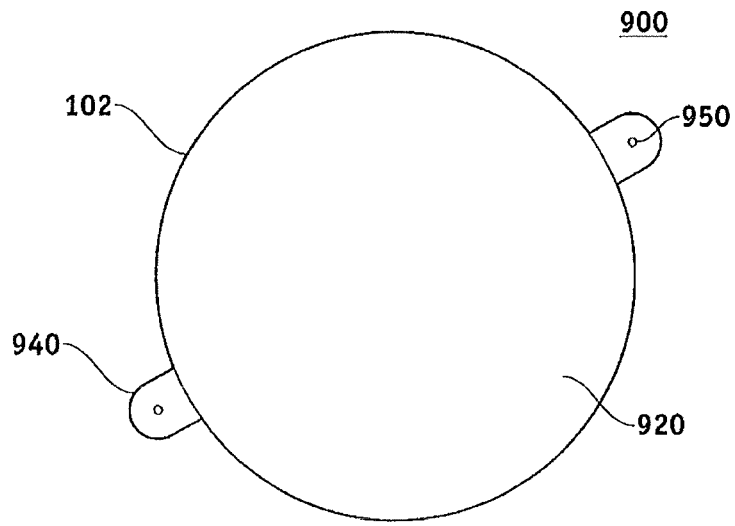
FIG. 9 illustrates an optic with a film coating a surface according to an aspect of the present invention.

Referring now to FIG. 9, there is shown optic 102 with a film coating the top surface thereof, according to an aspect of the present invention. As illustrated in FIG. 9, optic 102 is covered with mechanical film 920, rather than chemical coating 750. Film 920 may have the properties and/or aspects of coating 750, as discussed above, and may be mechanically removable from the lens during implantation, or may dissolve substantially simultaneously with implantation, for example.

Film 920 may have included thereon, as a part thereof, or attached thereto, at least one tab 940 (FIG. 9 shows two exemplary tabs 940, 950). Tab 940 may be an inert film that initially at least partially covers optic 710, such as to protect at least a part of the surface of optic 710. Tabs 940, 950 may readily enable film 920 to be removed after, or during, insertion of optic 710 into the eye. Such tab(s) 940, 950 may thus include coloring to enable the tab to be more clearly visible during the surgical process. Tabs 940, 950 may match the area of the removal tool. Further, tabs 940, 950 and film 920 may preferably be small to remove through the surgical incision discussed above.

Examples of material(s) for removable film 920 include one or more of the following: polyethylene terephthalate (PET), polytetrafluoroethylene (PTFE), polystyrene, polyethylene, polypropylene, polymethylmethacrylate, ethyl acrylate, ethyl methacrylate, 2,2,2-trifluoroethyl, and the like. In an embodiment, the film may include a copolymer of ethyl acrylate, ethyl methacrylate, and 2,2,2-trifluoroethyl methacrylate, cross-linked with ethylene glycol dimethacrylate. Incorporated within or under film 920 may be adherents, medications, or the like, as discussed hereinabove with respect to coating 750. Further, film 920 may be a type of coating as discussed herein. Coating 750 and film 920 may additionally be employed together, for example. As such, film 920 may provide protection, may allow for drug delivery for medications in coating 750 that may be reactive if not sealed from the air, may allow for coating 750 that does not provide protection of the optic, or may allow for coating that is sensitive during the surgical procedure, for example.

Film 920 may also be included on the haptic 104. Such film 920 may provide similar benefits to coating 750. For example, film 920 may differ as to the properties or thickness as between a film on optic 102 and haptic 104. Separate films 920 may be upon optic 102 and haptic 104. Separate coatings 750 independent from or associated with film 920 may deliver two stage medicinals, such as wherein one medicinal stage is on the optic, and the second stage is on the haptic. When placed together in the eye, the multi-part or multi-stage medicinal may combine to provide desired medicinal characteristics to the patient.

Additionally or alternatively, coating 750 and/or film 920 may be provided on the insertion tools discussed hereinthroughout. This coating 750 or film 920 may be similar to that described above for placement on the lens. Coating 750 or film 920 may include a broader range of potential materials, in part because mechanical, legal or technical requirements for coating surgical tools may be less stringent than those for coating an implanted optic. In particular, coatings on the tools may not be required to dissolve or be removed. Coating 750 or film 920 may reduce impacts of the tools on the lens and subsequent lens damage, and/or may increase the lubricity of the tools, such as to thereby reduce friction and/or tackiness of the lens during the insertion procedure.

Figure 10:
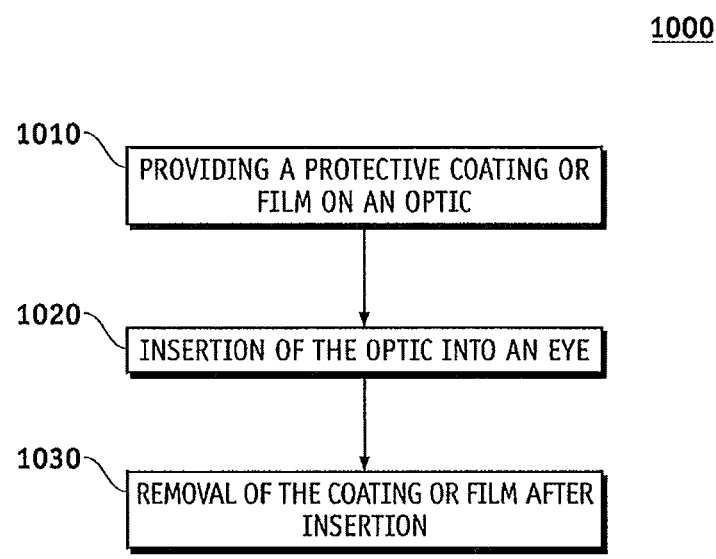
FIG. 10 illustrates a method of providing a protective coating on an optic according to an aspect of the present invention.

FIG. 10 illustrates a method 1000 of protecting a lens during surgical implantation, and/or of providing benefits to the implantation process. Method 1000 may include providing a protective coating or film on an optic at step 1010. Included within this film or coating, or underlying or overlaying same, may be an impregnating substance, such as medication, as discussed herein throughout. Method 1000 may further include insertion of the optic into an eye at step 1020. This insertion may include folding/unfolding, injecting, and the like, as described herein. Method 1000 may further include removal of the protective film or coating at step 1030. This removal may include physical removal during the surgical procedure, or may include dissolving or similar chemical processing, related to or unrelated to the surgical procedure, for example.

Figure 11:
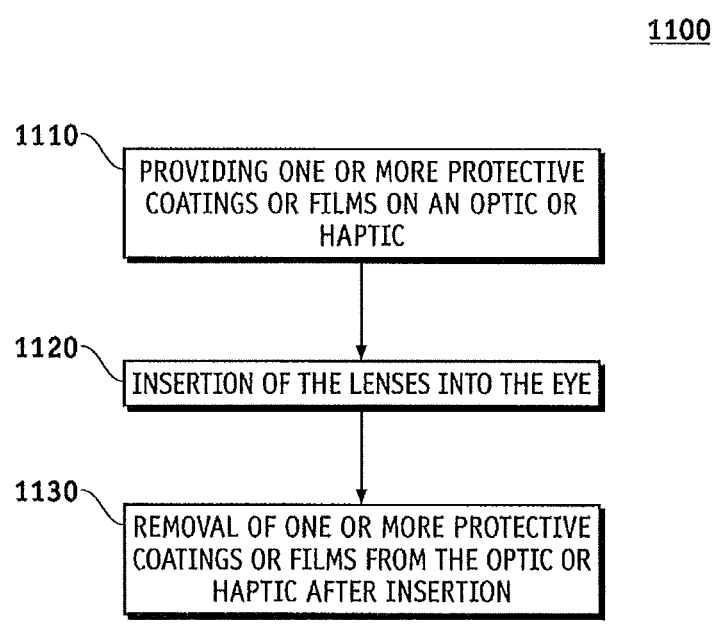
FIG. 11 illustrates a method of providing a protective coating on an optic and haptic according to an aspect of the present invention.

FIG. 11 illustrates a method 1100 of protecting a lens during surgical implantation, and/or of providing benefits to the implantation process. Method 1100 may include providing one or more protective coatings or films on an optic or haptic at step 1110. Included within this coating, film, or underlying or overlaying same, may be an impregnating substance, such as medication, as discussed herein throughout. Method 1100 may further include insertion of the lens into an eye at step 1120. This insertion may include folding/unfolding, injecting, and the like, as described herein. Method 1100 may further include removal of one or more of the protective coatings or films at step 1130. This removal may include physical removal during the surgical procedure, and/or may include dissolving or similar chemical processing, related to or unrelated to the surgical procedure, for example.

Although the invention has been described and pictured in an exemplary form with a certain degree of particularity, it is understood that the present disclosure of the exemplary form has been made by way of example, and that numerous changes in the details of construction and combination and arrangement of parts and steps may be made without departing from the spirit and scope of the invention as set forth in the claims hereinafter.

The invention claimed is:

1. A system, comprising:
an implantable lens having an optic;
a haptic coupled to the optic;
at least one haptic coating layer applied to at least one surface of the haptic; and
a first coating layer applied to at least one surface of the optic; and
a second coating layer applied to the first coating layer, wherein the second coating layer is different from the first coating layer, and wherein at least one of the first or the second coating layers comprises a biodegradable polymer comprising an impregnated medication.

2. The system of claim 1, wherein at least one of said first coating layer or said second coating layer is capable of removal following the implantation.

3. The system of claim 2, wherein the capability of removal comprises one selected from the group consisting of mechanical removability and chemical removability.

4. The system of claim 2, wherein the capability of removal comprises degradation over a predefined time period comprising one selected from the group consisting of a range of about a day to multiple years, and an approximation of a healing time from the implantation.

5. The system of claim 2, wherein the at least one of the first coating layer or the second coating layer on the optic comprises at least one of a color or a texture to aid in the removal of the at least one of the first coating layer or the second coating layer.

6. The system of claim 2, wherein the at least one of the first coating layer or the second coating layer on the optic comprises at least one tab to aid in the removal of the at least one of the first coating layer or the second coating layer.

7. The system of claim 1, further comprising at least one additional coating layer applied to a second surface of the optic, wherein said additional coating layer is capable of at least partially protecting the second surface of the optic.

8. The system of claim 1, wherein the application to the at least one surface of the optic comprises at least one selected from the group consisting of an adhesion, a contact force, and an impregnation.

9. The system of claim 1, wherein the at least one haptic coating layer comprises a lubricant.

10. The system of claim 1, wherein the at least one haptic coating layer is different than at least one of the first coating layer or the second coating layer on the optic.

11. The system of claim 1, wherein the first coating layer is configured to degrade over a first time period and the second coating layer is configured to degrade over a second time period different than the first time period.

12. The system of claim 11, wherein the first coating layer comprises an impregnated first medication and the second coating layer comprises an impregnated second medication different than the first medication.

13. The system of claim 12, wherein the impregnated second medication of the second coating layer is a first stage of a multi-stage medication and the impregnated first medication of the first coating layer is a second stage of the multi-stage medication.

14. The system of claim 1, wherein the second coating layer is separably attached to the first coating layer such that the second coating layer is configured to be separated following implantation.

15. The system of claim 1, wherein at least one of the first coating layer or the second coating layer has a variable thickness.

16. The system of claim 1, wherein the at least one haptic coating layer comprises a second medication.

* * * * *